US00PP35756P2

(12) United States Plant Patent
Hammett

(10) Patent No.: US PP35,756 P2
(45) Date of Patent: Apr. 16, 2024

(54) ***DAHLIA* PLANT NAMED 'KH72214-08'**

(50) Latin Name: *Dahlia variabilis*
Varietal Denomination: KH72214-08

(71) Applicant: Kiwi Flora Ltd., Aukland (NZ)

(72) Inventor: Keith Hammett, Aukland (NZ)

(73) Assignee: Kiwi Flora Ltd., Aukland (NZ)

( * ) Notice: Subject to any disclaimer, the term of this patent is extended or adjusted under 35 U.S.C. 154(b) by 0 days.

(21) Appl. No.: 18/185,370

(22) Filed: Mar. 17, 2023

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ..... A01H 5/02; A01H 5/00; A01H 6/14
See application file for complete search history.

(56) References Cited

U.S. PATENT DOCUMENTS

PP21,370 P2 * 10/2010 Kaagman ..... A01H 6/14 Plt./321
PP23,332 P2 * 1/2013 Hammett ..... A01H 6/14 Plt./321

OTHER PUBLICATIONS

Fletcher. Captivating 2023's New Annuals, Thursd blog, retrieved on Jul. 19, 2023 at https://thursd.com/posts/captivating-2023s-new-annuals, 2022, 20 pp. (Year: 2022).*
Plant Haven *Dahlia* Mystic Flares Dynamite, retrieved on Jul. 19, 2023 at https://archive.planthaven.com/plant/dahlia-mystic-flares-dynamite/, 2 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Dahlia* plant named 'KH72214-08' that is distinguishable by its compact upright plant habit, and dissected leaves and leaflets which are very dark green, almost black in color. The inflorescence of 'KH72214-08' is classified as a Collarette form of *Dahlia* in which a single outer whorl of bicolored orange and orange-red ray flowers, and an inner whorl of mauve-pink petaloid stamens, are arranged around a central cluster or disc of disc florets. The central disc of the inflorescence of 'KH72214-08' is initially dark red in color until the disc florets are fully developed and exhibit their dark yellow stigmas. After one year of growth, plants of 'KH72214-08' are 55 cm in height and 35 cm in width. 'KH72214-08' is hardy in USDA Zones 9 and higher.

2 Drawing Sheets

Figure 1:
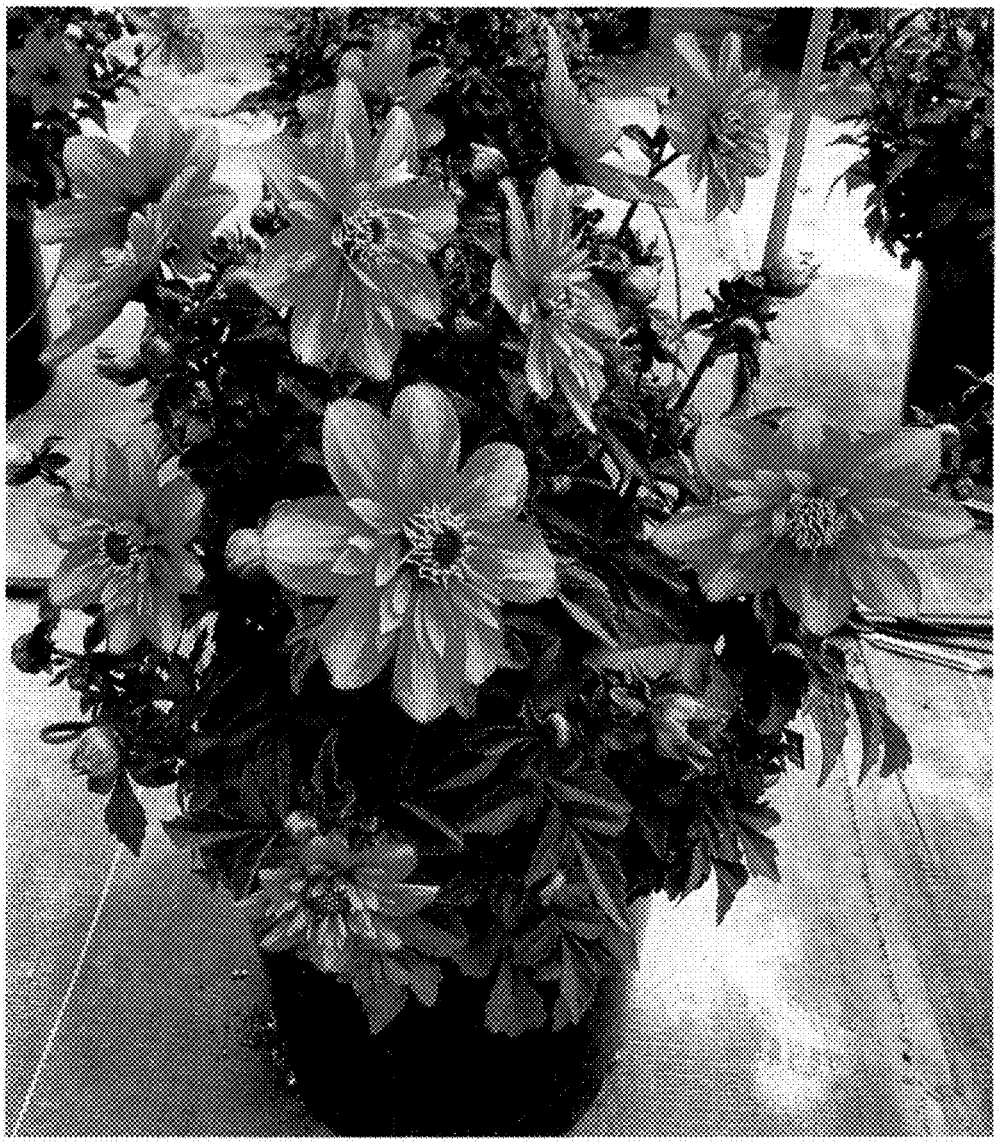

Genus and species:
Genus: *Dahlia variabilis*.
Variety denomination: 'KH72214-08'.

BACKGROUND OF THE NEW PLANT

The present invention relates to a new and distinct cultivar of *Dahlia* grown for use in containers, in mixed combinations, beds and in the landscape. The new invention is known botanically as *Dahlia variabilis* and will be referred to hereinafter by the cultivar name 'KH72214-08'.

The genus *Dahlia* is in the family Compositae. The inflorescence of 'KH72214-08' is classified as a Collarette form of *Dahlia* and consists of a single outer whorl of sterile ray flowers, and an inner whorl (the collar) of petaloid stamens, arranged around a central cluster or disc of disc florets.

In 2000, the inventor commenced a breeding program at the inventor's nursery in Auckland, New Zealand with the aim of developing dark-leafed *Dahlia* varieties which bear flowers classified as Collarette form. The inventor raised the new variety 'KH72214-08' by first sowing seeds of the inventor's internal hybrid known as *Dahlia* code number 72026-04 (unreleased, unpatented). The resulting seedlings were planted in a block adjacent to a block of assembled

*Dahlia* plants with Collarette flower forms. Seeds were collected from pollinated plants of *Dahlia* 72026-04, sown and grown-on to flowering stage, and evaluated for its qualities of flower appearance, darkness of foliage and overall plant habit. The inventor selected the new variety 'KH72214-08' for these qualities and especially for the vibrant bicolored orange and orange-red color combination of the ray floret petals.

The first asexual reproduction of 'KH72214-08' was conducted by the inventor in 2019 at the inventor's nursery in Auckland, New Zealand using softwood cuttings. The inventor has confirmed that 'KH72214-08' is a stable and uniform variety which reproduces true to type in subsequent generations of asexual propagation.

SUMMARY

The following traits have been repeatedly observed and represent the distinguishing characteristics of the new *Dahlia* cultivar named 'KH72214-08'. These traits in combination distinguish 'KH72214-08' from all other existing varieties of *Dahlia* known to the inventor. 'KH72214-08' has not been tested under all possible conditions and phenotypic differences may be observed with variations in environmental, climatic, and cultural conditions, however, without any variance in genotype.

1. 'KH72214-08' exhibits a compact upright plant habit.
2. 'KH72214-08' bears markedly dissected leaves and leaflets.
3. The leaves and leaflets of 'KH72214-08' are very dark green, almost black in color.
4. The inflorescence of 'KH72214-08' is classified as a Collarette form of *Dahlia* in which a single outer whorl of sterile ray flowers, and an inner whorl of petaloid stamens, are arranged around a central cluster or disc of disc florets.
5. The petals of the ray flowers of 'KH72214-08' are bicolored orange and orange-red.
6. The petaloid stamens of the ray flowers of 'KH72214-08' are light mauve-pink in color.
7. The central disc of the inflorescence of 'KH72214-08' is initially dark red in color until the disc florets are fully developed and exhibit their dark yellow exserted stigmas.
8. After one year of growth, plants of 'KH72214-08' are 55 cm in height and 35 cm in width.
9. 'KH72214-08' is hardy in USDA Zones 9 and higher.

COMPARISON WITH PARENTAL LINES AND KNOWN VARIETY

Whereas the ray florets of 'KH72214-08' are bicolored orange and orange-red, and the petaloid stamens of 'KH72214-08' are light mauve-pink in color, and the central disc of 'KH72214-08' is dark red in color, the female parent '72026-04' is also a Collarette form which bears crimson ray florets with paler crimson disc florets. In addition, 'KH72214-08' bears larger flowers than the female parent bears, and exhibits a more compact growth habit. The male parent of 'KH72214-08' is an unknown *Dahlia* variety of Collarette form.

'KH72214-08' may be distinguished from the Collarette varieties of *Dahlia, Dahlia* Plant named 'Dream Seeker' (unpatented) which was raised by the inventor, and *Dahlia* Plant named 'Golia Rosbi' (U.S. Plant Pat. No. 21,370). The ray florets and the petaloid stamens of 'Dream Seeker' are all bright saturated orange in color such that the inflorescence is not bicolored. The ray florets and petaloid stamens of 'Golia Rosbi' all exhibit the same coloration: bright red fading to pink or white towards their bases. In addition, 'Golia Rosbi' bears approximately one petaloid stamen per ray floret, whereas 'KH72214-08' bears four petaloid stamens per ray floret. The ray florets and the petaloid stamens of 'KH72214-08' exhibit different colors such that the numerous mauve-pink petaloid stamens are presented as an inner collar or ruff which contrasts with the orange and orange-red ray florets.

'KH72214-08' may be distinguished from non-Collarette varieties of *Dahlia* by the presence or absence of a prominent inner whorl of petaloid stamens. For example, the inventor's variety *Dahlia* 'Mystic Enchantment' (U.S. Plant Pat. No. 23,332) does not bear any petaloid stamens. The inflorescence of 'Mystic Enchantment' is entirely bright red in color.

BRIEF DESCRIPTION OF THE PHOTOGRAPHS

Figure 2:
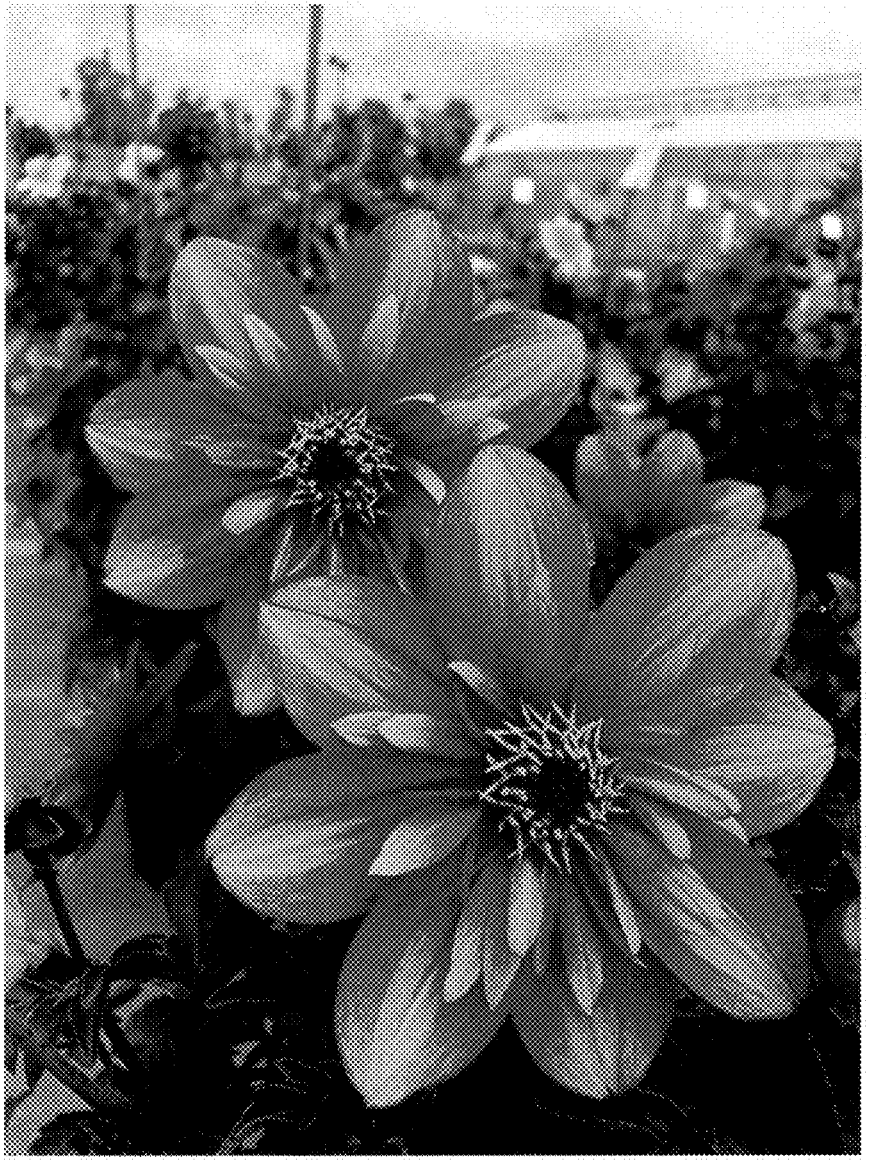

The accompanying color drawings labeled FIG. 1 and FIG. 2 illustrate the overall appearance of the new *Dahlia* cultivar named 'KH72214-08' showing the colors as true as is reasonably possible to obtain in colored reproductions of this type. Colors in the photographs may differ from the color values cited in the detailed botanical description, which accurately describes the actual colors of the 'KH72214-08'. The photographs were made from digital photographs of twelve four months old from a cutting plant grown outdoors in Santa Barbara, California.

The drawing labeled FIG. 1 depicts the entire plant in bloom.

The drawing labeled FIG. 2 depicts a close-up view of the face of a flower of 'KH72214-08'.

BOTANICAL DESCRIPTION OF THE PLANT

The following is a detailed botanical description of the new *Dahlia* cultivar named 'KH72214-08'. Observations and measurements were collected in late August 2022 in Santa Barbara, California from a 12 month old plant grown out of doors in a 2-gallon container. Color determinations were made in accordance with The 2007 Royal Horticultural Society Colour Chart from London, England, except where general color terms of ordinary dictionary significance are used. Growing requirements are similar to the species.

Botanical classification:

*Classification of flower* (*inflorescence*).—Collarette.
*Family*.—Compositae.
*Genus and species*.—*Dahlia variabilis*.
*Denomination*.—'KH72214-08'.
*Common name*.—*Dahlia*.

Parentage:

*Female parent*.—*Dahlia* code number 72026-4.
*Male parent*.—The identity of the male parent is unknown.

Plant:

*Propagation method*.—Tissue culture and cuttings from virus-indexed mother stock.
*Rooting system*.—Fine and fibrous.
*Vigor*.—Vigorous, naturally self-branching.
*Habit*.—Upright habit.
*Use*.—For use in containers, in mixed combinations, beds and the landscape.
*Type*.—Annual in most regions, perennial in USDA Zone 9 and warmer.
*Dimensions at* 12 *months of age from a cutting*.—55 cm in height, 35 cm in width.
*Cultural requirements*.—Grow in full sun with regular water, and well-draining potting soil.
*Pest susceptibility*.—Susceptible to aphids (*Aphis gossypii*) when stressed.
*Disease susceptibility*.—Susceptible to powdery mildew (*Erysiphacea* spp.) in humid conditions.
*Hardiness*.—USDA Zone 9 and higher.

Stem:

*Shape*.—Cylindrical.
*Dimensions*.—3 cm-5 cm length, 11 mm in diameter at base.
*Color*.—Ranges between 187A and 187B.
*Surface*.—Glabrous.

Branches:

*Number*.—3-5 basal branches arise from the stem, 6 or more secondary branches borne on each basal branch.
*Internode distance*.—3.5 cm-7 cm.

Foliage:

*Type*.—Compound, 5 leaflets, each leaflet dissected into three lobes.

*Leaf arrangement*.—Opposite.

*Leaflet arrangement*.—One lowermost opposite pair, one central opposite pair, one single terminal leaflet. Central leaflet pair and single terminal leaflet all joined at base.

*Leaf wings*.—Absent.

*Leaf and leaflet division*.—Simple.

*Leaf shape* (*overall*).—Hastate.

*Leaflet shape*.—Lobed, lobes obovate.

*Leaf dimensions* (*overall*).—12 cm in length, 9 cm in width across lowest leaflets.

*First* (*lowest*) *leaflet dimensions*.—5.5 cm in length, 2.5 cm in width.

*Second* (*central*) *leaflet dimensions*.—4 cm in length, 2 cm in width.

*Terminal leaflet dimensions*.—5.5 cm in length, 3.5 cm in width.

*Leaf and leaflet color* (*adaxial surfaces*).—N186A, greener in shade, towards 189A; darker in sun or when first emerging, towards 202A.

*Leaf and leaflet color* (*abaxial surfaces*).—138B.

*Leaf and leaflet margins*.—Minutely serrate, incisions 0.5 mm-1.0 mm apart, 0.5 mm in depth, serrations finely ciliate, tiny, less than 0.5 mm in length, color NN155D.

*Leaf and leaflet apex*.—Acute.

*Leaf and leaflet base*.—Truncate.

*Leaf and leaflet venation pattern*.—Pinnate.

*Vein color*.—Adaxial surface: As leaf except midrib 183D. Abaxial surfaces: Midrib 152A, lateral veins N137A.

*Leaf and leaflet surfaces* (*abaxial surfaces*).—Glabrous, matte.

*Leaf and leaflet surfaces* (*adaxial surfaces*).—Lightly pubescent, hairs 0.5 mm in length, color NN155D.

*Leaf attachment*.—Petiolate to first leaflet pair, petiole continues to base of second leaflet pair.

Petiole:

*Shape*.—Sulcate.

*Dimensions* (*stem to first leaflet pair*).—2.5 cm in length, 3 mm - 4 mm in width, 2 mm in depth.

*Dimensions* (*between first and second leaflet pairs*).—3 cm in length, 2 mm in width, 1.5 mm in depth.

*Color* (*adaxial surface*).—187A.

*Color* (*abaxial surface*).—152D.

*Surface*.—Faintly puberulent.

Inflorescence:

*Inflorescence type*.—Capitulum on each branch, classified as "collarette" form consisting of a single outer whorl of sterile ray flowers, an inner whorl (the collar) of petaloid stamens, arranged around a central cluster or disc of disc florets.

*Aspect*.—Facing upward and outward.

*Inflorescence quantity*.—15-20 colored buds and opening and open flowers at peak flowering.

*Dimensions of inflorescence* (*average*).—9.5 cm in diameter and 2.0 cm in depth.

*Inflorescence shape*.—Radiate with center disk.

*Blooming seasons*.—Summer and fall.

*Lastingness of inflorescence*.—8-10 days until petal fall.

Peduncle:

*Dimensions* (*average*).—20 cm in length and 0.3 cm-0.4 cm in diameter.

*Shape*.—Cylindrical.

*Surface*.—Glabrous.

*Color*.—N186C.

Receptacle:

*Receptacle dimensions*.—7 mm in height, 13 mm in diameter.

*Receptacle surface*.—Glabrous.

*Receptacle color*.—147A.

Phyllaries:

*Description*.—Two whorls of phyllaries, or involucral bracts, subtend the receptacle. An inner uppermost whorl consists of eight membranous translucent phyllaries adpressed to the abaxial surface of each ray floret petal. A second outer whorl of phyllaries is attached at the base of the inner whorl. Phyllaries in the outer wall are free and strongly reflexed.

*Inner phyllaries*.—Number: 12 (6 large, 6 small). Shape: Broadly lanceolate. Dimensions (larger phyllaries): 20 mm in length and 8 mm in width. Dimensions (small phyllaries): 11 mm in length and 3 mm-6 mm in width. Texture: Membranous, translucent towards apex. Color (adaxial and abaxial surfaces): 160A at base becoming lighter towards apex, closest to 160D but lighter. Veins (both surfaces): Fine longitudinal parallel veins, vein color 53A. Apex: Rounded. Base: Truncate. Margin: Entire. Surface (both surfaces): Glabrous, waxy.

*Outer phyllaries*.—Number: 5 or 6 in number. Shape: Obovate, reflexed. Dimensions: 17 mm in length, 9 mm in width. Color (both surfaces): 147A. Apex: Obtuse. Base: Truncate. Margin: Entire. Surface (both surfaces): Glabrous, glossy, leathery.

Bud:

*Shape*.—Oblate.

*Dimensions* (*sepals about to open*).—13 mm in height and 16 mm in diameter.

*Surface*.—Glabrous, glossy.

*Color*.—152D with fine longitudinal parallel veins on sepal abaxial surface, vein color 53A.

*Apex*.—Obtuse.

*Base*.—Truncate.

Ray florets:

*Petals*.—Quantity per inflorescence: 8. Arrangement: Radiate. Dimensions (average): 40 mm in length and 22 mm in width. Shape: Obovate. Profile (upper surface, lateral cross-section at mid-point between base and apex): Initially slightly concave becoming planar when fully expanded. Profile (upper surface, longitudinal cross-section at leaf axis): Moderately convex. Overlapping: Ray florets overlap from base to approximate mid-point and are non-overlapping from mid-point to apex. Apex: Obtuse with minute apical notch. Base: Cuneate. Margin: Entire. Margin rolling: Moderately involute at apex and towards apex; otherwise no rolling. Colors: Petals consist of three longitudinally fused lobes of approximately equal width. Central petal lobe (adaxial surface): 28C with veins color 33A. Outer petal lobes (adaxial surface): 33A. All lobes (abaxial surface): 45C. Veins (adaxial): Fine, parallel, visible in central lobe only, color 33A. Veins (abaxial): Faint, color as petal 45C. Surface: All lobes glabrous, matte. Central lobe adaxial surface depressed, central lobe abaxial surface raised.

Petaloid stamens:

*Quantity per ray floret.*—4 (2 large, 2 small), all basally fused.

*Dimensions* (*large petaloid stamens*).—22 mm in length, 5 mm in width.

*Dimensions* (*small petaloid stamens*).—12 mm in length, 2 mm in width.

*Shape*.—Lanceolate.

*Apex*.—Acute.

*Base*.—Cuneate.

*Margin*.—Entire.

*Colors* (*both surfaces*).—62B becoming lighter 62D towards apex.

*Surface* (*both surfaces*).—Glabrous, matte.

Disc florets:

*Description*.—Disc florets massed in the center of the receptacle to form the central inflorescence disc. Younger inner disc florets (stigmas not exposed) exhibit dark purple fused petal corollas. Fully developed disc florets exhibit prominently exserted yellow bifurcated stigmas.

*Disc diameter.*—22 mm.

*Disc color*.—Initially, dark red 53A (only young disc floret petals visible) becoming deep yellow 17B as disc florets open (from circumference then inwards) and the yellow stigmas become prominent.

*Quantity of disk florets.*—80-90 per inflorescence.

*Dimensions, including base and corolla tube.*—9 mm-12 mm in length, 3 mm in diameter at corolla tube apex, 1 mm in diameter at tube base.

*Petals, corolla tube.*—5 petals, longitudinally fused to form corolla tube.

*Corolla tube*.—Shape: Tubular, petal apices free and flared, apex acute. Dimensions: 8 mm-9 mm in length. Color (petals, tube, both surfaces): 53A. Surface: Glabrous, glossy.

*Disc floret sepals*.—Quantity, arrangement: Approximately 75 mostly wrapping around corolla tube. Shape: Lanceolate. Dimensions: 7 mm-11 mm in length, 3 mm-6 mm in width. Texture: Membranous, translucent. Color (both surfaces): Closest to 151D but lighter. Veins (both surfaces): Fine longitudinal parallel veins towards apex only, vein color 53A. Apex: Rounded. Base: Truncate. Margin: Entire. Surface (both surfaces): Glabrous, waxy.

Reproductive organs (present on disc florets only):

*Stamens.*—5 in number, fused at base.

*Filament dimensions.*—3 mm in length, less than 0.5 mm in diameter.

*Filament color.*—152C.

*Anther*.—Absent.

*Pollen*.—None present.

*Pistil*.—One present.

*Style dimensions.*—13 mm in length, 0.5 mm in diameter.

*Style color.*—4C.

*Stigma form*.—Bifurcated and prominently exserted, 2 mm above corolla tube apex.

*Stigma dimensions* (*each arm*).—3 mm in length, 0.5 mm in diameter.

*Stigma color.*—17B.

*Ovary position*.—Inferior.

*Ovary color.*—*N*144A.

*Ovary shape*.—Globose.

*Ovary dimensions.*—1.5 mm in diameter.

Seed: None observed.

I claim:

1. A new and distinct cultivar of *Dahlia* Plant Named 'KH72214-08' as described and illustrated herein.

* * * * *